United States Patent
Zhou et al.

(10) Patent No.: US 8,121,360 B2
(45) Date of Patent: Feb. 21, 2012

(54) COMPUTER AIDED DETECTION AND DECISION SUPPORT

(75) Inventors: Xiang Zhou, Exton, PA (US); Alok Gupta, Bryn Mawr, PA (US); Arun Krishnan, Exton, PA (US); Jörg Freund, München (DE); Dorin Comaniciu, Princeton Junction, NJ (US)

(73) Assignees: Siemens Medical Solutions USA, Inc., Malvern, PA (US); Siemens Aktiengesellschaft, Munich (DE); Siemens Corporation, Iselin, NJ (US)

( * ) Notice: Subject to any disclaimer, the term of this patent is extended or adjusted under 35 U.S.C. 154(b) by 985 days.

(21) Appl. No.: 11/782,694

(22) Filed: Jul. 25, 2007

(65) Prior Publication Data

US 2008/0037852 A1  Feb. 14, 2008

Related U.S. Application Data

(60) Provisional application No. 60/834,444, filed on Jul. 31, 2006.

(51) Int. Cl.
  *G06K 9/00* (2006.01)
(52) U.S. Cl. .................. 382/128; 382/133; 382/156
(58) Field of Classification Search .................. 382/128, 382/132, 228, 232, 100, 278, 224, 133, 156, 382/159; 705/2; 702/20; 706/19, 20, 45
See application file for complete search history.

(56) References Cited

U.S. PATENT DOCUMENTS

| | | | | |
|---|---|---|---|---|
| 6,470,092 B1* | 10/2002 | Li et al. | ............ | 382/132 |
| 7,194,119 B2* | 3/2007 | Zahlmann et al. | ............ | 382/128 |
| 7,478,091 B2* | 1/2009 | Mojsilovic et al. | ............ | 382/128 |
| 7,558,427 B2* | 7/2009 | Schmidt et al. | ............ | 382/228 |
| 7,739,053 B2* | 6/2010 | Palenchar et al. | ............ | 702/19 |
| 7,747,050 B2* | 6/2010 | Lau et al. | ............ | 382/128 |
| 2001/0043729 A1* | 11/2001 | Giger et al. | ............ | 382/128 |
| 2004/0101177 A1* | 5/2004 | Zahlmann et al. | ............ | 382/128 |
| 2005/0149360 A1* | 7/2005 | Galperin | ............ | 705/2 |
| 2008/0027917 A1* | 1/2008 | Mukherjee et al. | ............ | 707/3 |

* cited by examiner

*Primary Examiner* — Daniel Mariam
*Assistant Examiner* — Nancy Bitar
(74) *Attorney, Agent, or Firm* — Peter Robert Withstandley

(57) ABSTRACT

A system for computer aided detection and decision support includes an ontology of image representations for injecting meaning into and adding relationships among image contents, an image understanding and parsing module in communication with the ontology of image representations for extracting structures from an image including the image contents, and a reasoning engine based in communication with the ontology and the image understanding and parsing module for classifying the image contents, wherein the system receives the image and corresponding descriptive information.

8 Claims, 3 Drawing Sheets

COMPUTER AIDED DETECTION AND DECISION SUPPORT

CROSS-REFERENCE TO RELATED APPLICATION

This application claims priority to U.S. Provisional Application Ser. No. 60/834,444, filed on Jul. 31, 2006, which is herein incorporated by reference in its entirety.

BACKGROUND OF THE INVENTION

1. Technical Field

The present invention relates to computer aided detection, and more particularly to a system and method for computer aided detection and decision support based on anatomical and functional understanding of medical images.

2. Discussion of Related Art

Current CAD (computer aided detection) and DSS (decision support system) systems are designed with specific domain constraints, assuming available the right images, imaging parameters, and disease context (mammography CAD for screening, lung CAD for nodule detection, colon CAD for polyp detection, etc.). They are very effective if all assumptions hold true.

However, they are "fragile" in the sense that if any one of the assumptions fails, the system produces unpredictable results, which may, in some cases, cause a potential risk or hazard.

Therefore, a need exists for a computer aided detection and decision support based on anatomical and functional understanding of medical images.

SUMMARY OF THE INVENTION

According to an embodiment of the present disclosure, a system for computer aided detection and decision support includes an ontology of image representations for injecting meaning into and adding relationships among image contents, an image understanding and parsing module in communication with the ontology of image representations for extracting structures from an image including the image contents, and a reasoning engine based in communication with the ontology and the image understanding and parsing module for classifying the image contents, wherein the system receives the image and corresponding descriptive information.

According to an embodiment of the present disclosure, a system for computer aided detection and decision support includes a memory device storing a plurality of instructions embodying a computer aided detection and decision support system, a processor for receiving an image including an object of interest and corresponding descriptive information and executing the plurality of instructions to perform a method including determining a segmentation of the image including the object of interest, detecting the object of interest, comparing the image including the object of interest to a knowledge model to determine an analysis of the object of interest, performing a similar case search against a picture archiving and communication system database based on a detected object of interest and the analysis, and outputting at least one image retrieved from the picture archiving and communication system database together with corresponding descriptive information.

According to an embodiment of the present disclosure, a computer readable medium is provided embodying instructions executable by a processor to perform a method for computer aided detection and decision support, the method including receiving an image including an object of interest and corresponding descriptive information, determining a segmentation of the image including the object of interest, detecting the object of interest, comparing the image including the object of interest to a knowledge model to determine an analysis of the object of interest, performing a similar case search against a picture archiving and communication system database based on a detected object of interest and the analysis, and outputting at least one image retrieved from the picture archiving and communication system database together with corresponding descriptive information.

BRIEF DESCRIPTION OF THE DRAWINGS

Preferred embodiments of the present invention will be described below in more detail, with reference to the accompanying drawings.

DETAILED DESCRIPTION OF EXEMPLARY EMBODIMENTS

Figure 1:
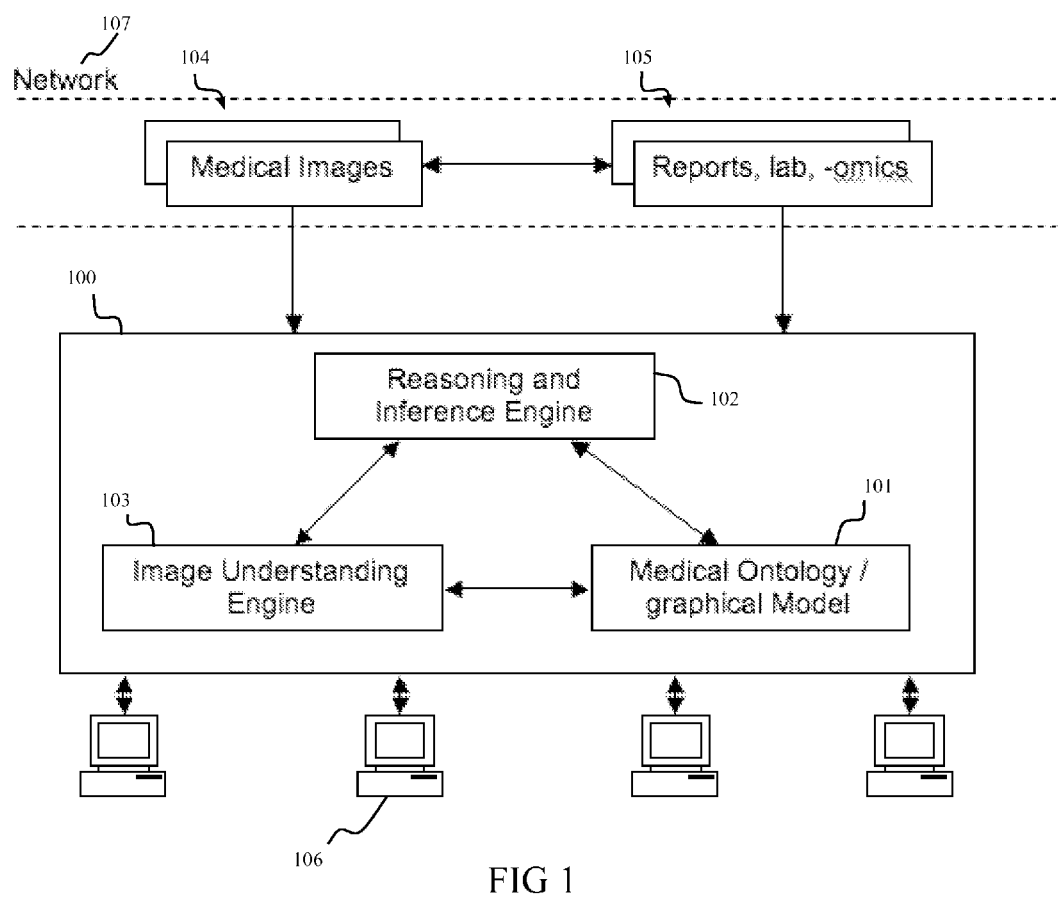
FIG. 1 is a diagram of a guided CAD/DSS system according to an embodiment of the present disclosure.

According to an embodiment of the present disclosure, image understanding techniques utilizing anatomical, physiological and pathological knowledge are used enhance the robustness, sensitivity/specificity, and broader applicability of an CAD/DSS system.

An exemplary CAD/DSS system 100 includes a representation of medical image contents module 101, medical image understanding and parsing module 102, and a reasoning, inference, or discover engine 103 based on the representation of medical image contents 101 and the medical image understanding and "parsing" module 102.

The CAD/DSS system 100 takes an input image(s) 104 and other information 105, for example, reports describing a patient who is the subject of the image(s), as input and serves results to a terminal or computer 106. The input image(s) 104 and other information 105 may be stored locally on the computer 106 or on a network 107.

The representation of medical image contents module 101 injects meaning into, and adds relationships among, features of the image(s) 104. The domain of the medical image contents module 101 may be constrained, for example, to human anatomy or even a particular portion of human anatomy.

The CAD/DSS system 100 may link models of anatomical, functional and biological structures or processes, for example, by injecting relative positions, related functions, other relationships, etc. Further, the CAD/DSS system 100 may include a component for capturing various evolutions of the hierarchy.

Linked models of anatomical, functional and biological structures or processes of the human body to contents extractable from heterogeneous medical images additional infrastructure (e.g., hardware/software and database schema, etc.) may be used support such a content representation and searching scheme.

The component for capturing various evolutions of the hierarchy further captures the physiological and pathological changes of the human body, evolving imaging technology, and discovery of new medical knowledge.

The module for medical image understanding and parsing 102 segments or interprets the medical image, according to one or more of anatomical or functional components.

According to an exemplary embodiment of the present disclosure, a trainable medical image parser may take a medical image as input and automatically parse it into segments that are meaningful in a clinical setting (e.g., cells, tissues, organs, organ systems, etc.).

According to an exemplary embodiment of the present disclosure, data organization in PACS (picture archiving and communication systems) based on image contents may use the system.

According to an exemplary embodiment of the present disclosure, the guided CAD/DSS may be implemented for a medical image search engine, e.g., for pharmaceutical recruiters, medical statisticians, and government agencies, etc. User groups beyond the medical domain may benefit as well. For example, pharmaceutical companies may use the guided CAD/DSS system for better-targeted patient recruitment for clinical trials, or more informative trial data analysis, government and research institutions may use the guided CAD/DSS system for more sensitive epidemiological studies, and insurance companies may use the guided CAD/DSS system for more automated treatment outcome analysis by insurance companies.

According to an exemplary embodiment of the present disclosure, the guided CAD/DSS may be implemented for a medical image search engine for radiology and cardiology using a medical ontology, wherein a user can submit keyword (s) or images as queries, and get back similar images that may not have the same exact words in its annotations, but is deemed similar either by the ontology, or by contents extracted from the query image.

For cancer staging, semantic support may be provided for organ-aware primary tumor detection, model-guided TNM (tumor-node-metasis) staging, semantic data alignment for change detection, etc.

For organ-aware primary tumor detection, with anatomical parsing of organs, different organ-specific CAD tools can be applied for the detection of the primary tumor.

Figure 2:
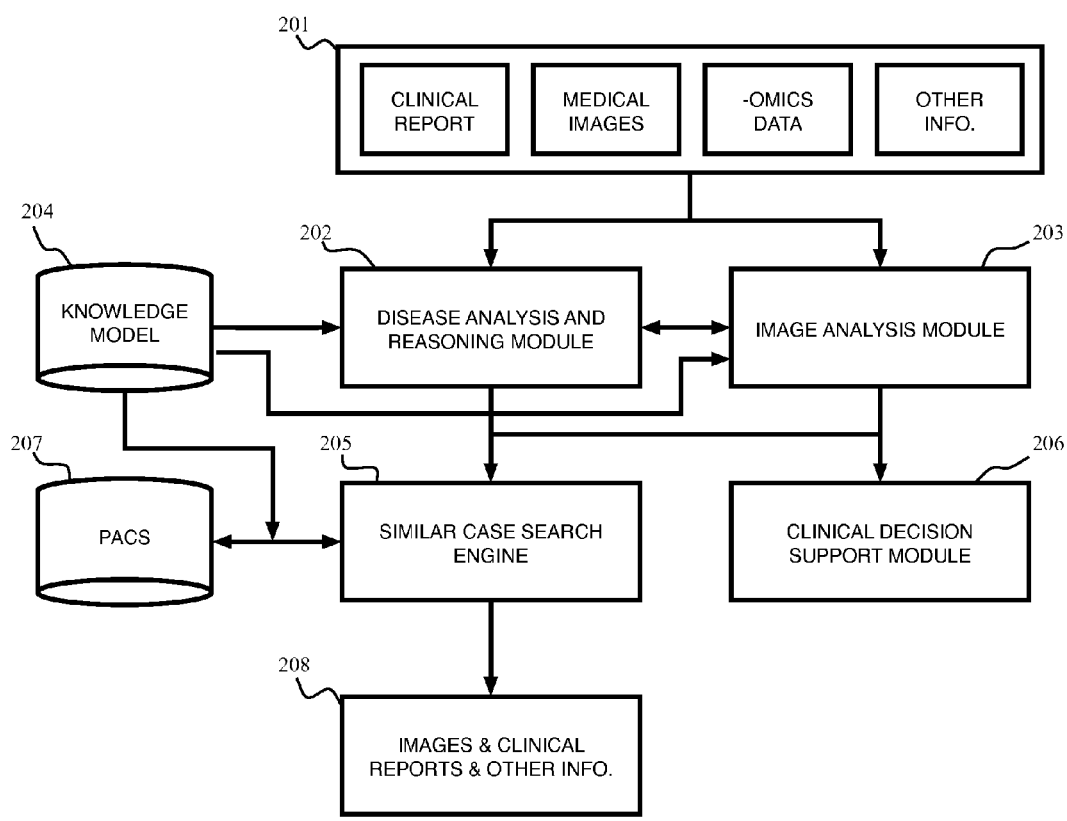
FIG. 2 is a flow chart of a method for guided CAD/DSS according to an embodiment of the present disclosure.

Referring to FIG. 2, for an exemplary implementation, model-guided TNM staging may be performed with a disease ontology and a tumor evolution model. TNM staging can be performed proactively in the most likely organs, achieving increased sensitivity and specificity.

In the example, a doctor treating a lung cancer patient may want to detect at what stage the cancer is and have similar cases returned, e.g., cases at a similar stage and having a similar prognosis. Data 201 including for example, clinical reports, medical images, etc. is input to a disease analysis and reasoning module 202 and an image analysis module 203. The disease analysis and reasoning module 202 determines, for example, that a sub-carinal node is involved but not the liver by comparing the data 201 to a knowledge model 204, e.g., a staging model for lung cancer selected from a plurality of different models. The knowledge model 204 for the example may include a human anatomical model related to lung cancer, e.g., a TNM lung cancer model. The knowledge model 204 may be selected automatically based on descriptive information, e.g., indicating a lung image, or manually. The image analysis module 203, which has access to the knowledge model 204, determines an organ segmentation and performed computer aided detection of lesions, lymph nodes, etc. The output of the disease analysis and reasoning module 202 and the image analysis module 203 are input to a similar case search engine 205 and a clinical decision support module 206. By accessing a PACS database, a similar case search may be performed based on the TNM cancer stage model, provided by the knowledge model 204. The similar case search engine 205 returns images, clinical reports, etc. for similar cases, e.g., an N2 stage lung cancer patient with a certain -omic signature (e.g., genomic, proteinomic, etc.). The clinical decision support module 206 outputs a determined stage of the lung cancer, e.g., N2 stage lung cancer. One of ordinary skill in the art would recognize that the system and method described with respect to FIG. 2 may be implemented in differently from the lung cancer example described above.

The semantic data alignment for change detection enables estimation of disease progressing, or monitoring of therapy response.

For cardiology, a unique aspect is the motion characteristics of the heart. Semantic queries related to cardiac motion, for example, regarding cardiovascular diseases, will be implemented and validated for different segmental conditions.

Since cardiac motion signatures are high-dimensional, spatially varying and difficult to localize, thus difficult to align, it can be a challenging target for semantic and generic abstraction and representation. Segmental coding convention in cardiology can be used as an initial guide. However, its limitation may call for new representations that code not only motion magnitude but also orientation.

For an exemplary implementation one or all of the following options can be implemented. Hierarchical representation of anatomical structures and functional dependencies (from cell to tissue to organ to system), cross-indexing of physiological and pathological contents, flexible indexing structure for easy adaptation to evolution (of human growth, of imaging technology, and of medical research), and speed-up schemes, e.g., fast (approximate) nearest neighbor search.

A guided CAD/DSS system according to an embodiment of the present disclosure can serve user groups including medical doctors for image-guided diagnosis and decision support, medical IT professionals for image-enabled advanced medical applications, pharmaceutical applications specialists for image-assisted patient recruitment and data analysis, patients and citizens for patient-centric information sharing, with image-enabled health/disease education, disease prevention, therapy/care selection—All to achieve distributed, informed and personalized health decisions, and policy makers for faster and better policy making from both the public policy (by the government) and insurance policy (by public or private insurance companies) points of view.

It is to be understood that the present invention may be implemented in various forms of hardware, software, firmware, special purpose processors, or a combination thereof. In one embodiment, the present invention may be implemented in software as an application program tangibly embodied on a program storage device. The application program may be uploaded to, and executed by, a machine comprising any suitable architecture.

Figure 3:
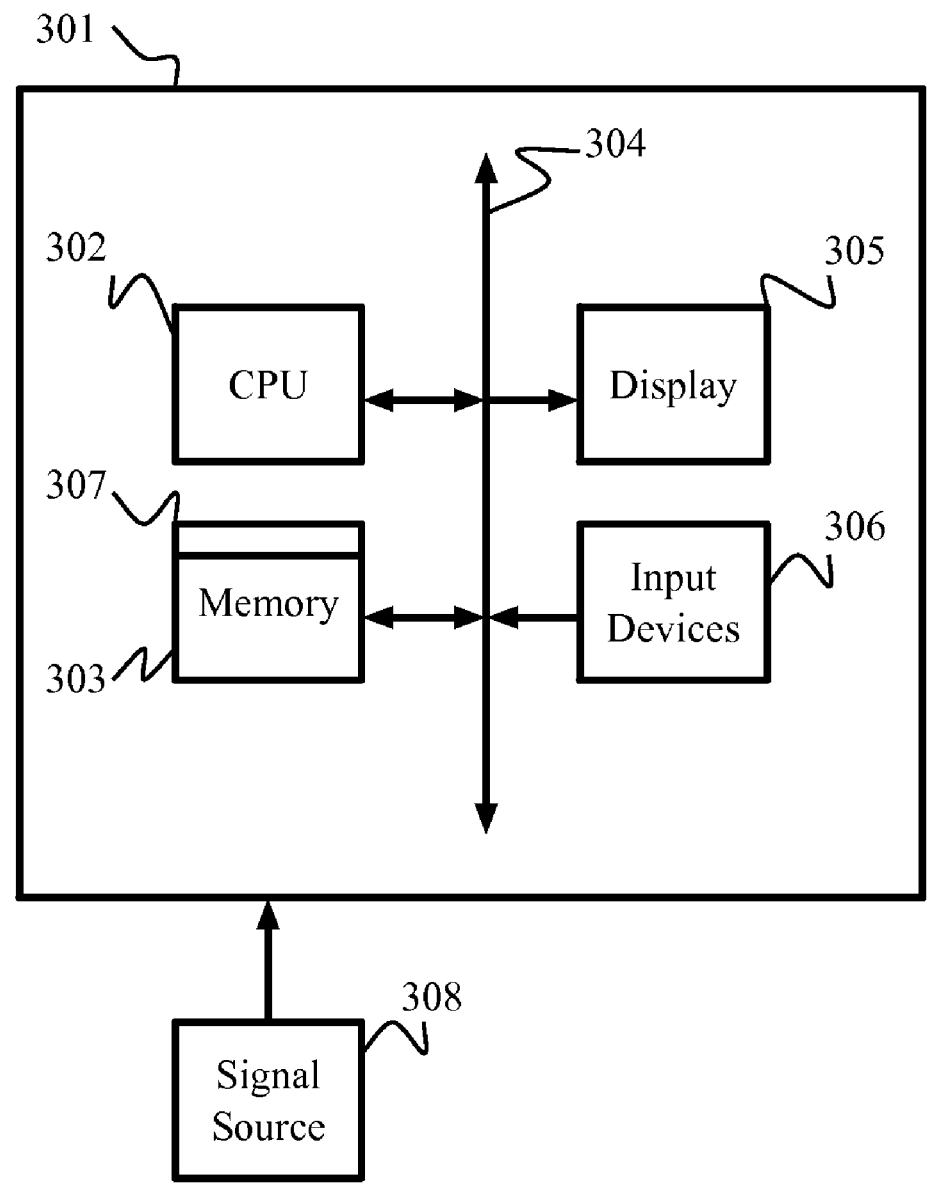
FIG. 3 is a diagram of a system according to an embodiment of the present disclosure.

Referring to FIG. 3, according to an embodiment of the present invention, a computer system 301 for guided CAD/DSS can comprise, inter alia, a central processing unit (CPU) 302, a memory 303 and an input/output (I/O) interface 304. The computer system 301 is generally coupled through the I/O interface 304 to a display 305 and various input devices 306 such as a mouse and keyboard. The support circuits can include circuits such as cache, power supplies, clock circuits, and a communications bus. The memory 303 can include random access memory (RAM), read only memory (ROM), disk drive, tape drive, etc., or a combination thereof. The present invention can be implemented as a routine 307 that is stored in memory 303 and executed by the CPU 302 to process a signal, e.g., a closed surface mesh, from the signal source 308. As such, the computer system 301 is a general purpose computer system that becomes a specific purpose computer system when executing the routine 307 of the present invention. The computer system 301 may further include a GPU 309 for processing certain operations.

The computer platform 301 also includes an operating system and micro instruction code. The various processes and functions described herein may either be part of the micro instruction code or part of the application program (or a combination thereof) which is executed via the operating system. In addition, various other peripheral devices may be connected to the computer platform such as an additional data storage device and a printing device.

It is to be further understood that, because some of the constituent system components and method steps depicted in the accompanying figures may be implemented in software, the actual connections between the system components (or the process steps) may differ depending upon the manner in which the present invention is programmed. Given the teachings of the present invention provided herein, one of ordinary skill in the related art will be able to contemplate these and similar implementations or configurations of the present invention.

Having described embodiments for a system and method for guided CAD/DSS, it is noted that modifications and variations can be made by persons skilled in the art in light of the above teachings. It is therefore to be understood that changes may be made in the particular embodiments of the invention disclosed which are within the scope and spirit of the invention as defined by the appended claims. Having thus described the invention with the details and particularity required by the patent laws, what is claimed and desired protected by Letters Patent is set forth in the appended claims.

What is claimed is:

1. A system for computer aided detection and decision support comprising:
    a memory device storing a plurality of instructions embodying a computer aided detection and decision support system;
    a processor for receiving an image of a patient including an object of interest and non-image data about the patient that is not encoded with the image data, and executing the plurality of instructions to perform a method comprising:
    determining a segmentation of the image including the object of interest;
    detecting the object of interest;
    automatically selecting a pre-defined disease analysis model from a database based upon the detected object of interest and the non-image data;
    comparing the image including the object of interest to the selected pre-defined disease analysis model to determine an analysis of the object of interest;
    performing a similar case search against a picture archiving and communication system database based on the detected object of interest and the analysis; and
    outputting at least one image retrieved from the picture archiving and communication system database together with corresponding descriptive information.

2. The system of claim 1 further comprising selecting the selected pre-defined disease analysis model according to a feature of the image.

3. The system of claim 1, wherein the non-image data comprises a clinical report.

4. The system of claim 1, wherein the non-image data comprises a relevant -omic signature.

5. A non-transitory computer readable medium embodying instructions executable by a processor to perform a method for computer aided detection and decision support, the method comprising:
    receiving an image including an object of interest and non-image data that is not encoded with the image data;
    determining a segmentation of the image including the object of interest;
    detecting the object of interest;
    automatically selecting a pre-defined disease analysis model from a database based upon the detected object of interest and the non-image data;
    comparing the image including the object of interest to the selected pre-defined disease analysis model to determine an analysis of the object of interest;
    performing a similar case search against a picture archiving and communication system database based on a detected object of interest and the analysis; and
    outputting at least one image retrieved from the picture archiving and communication system database together with non-image data.

6. The computer readable medium of claim 5, further comprising selecting the selected pre-defined disease analysis model according to a feature of the image.

7. The computer readable medium of claim 5, wherein the non-image data comprises a clinical report.

8. The computer readable medium of claim 5, wherein the non-image data comprises a relevant -omic signature.

* * * * *